United States Patent [19]

Plummer et al.

[11] Patent Number: 4,552,892
[45] Date of Patent: Nov. 12, 1985

[54] ACARICIDAL DIFLUOROETHENYLCYCLO-PROPANECARBOXYLATES

[75] Inventors: Ernest L. Plummer, Yardley; John F. Engel, Washington Crossing, both of Pa.; Richard B. Phillips, Cranbury, N.J.

[73] Assignee: FMC Corporation, Philadelphia, Pa.

[21] Appl. No.: 726,305

[22] Filed: Apr. 25, 1985

Related U.S. Application Data

[63] Continuation of Ser. No. 474,366, Mar. 11, 1983, abandoned.

[51] Int. Cl.$^4$ .................. C07C 69/743; A01N 53/00
[52] U.S. Cl. ................... 514/531; 514/510; 560/124
[58] Field of Search .................. 560/124; 514/531

[56] References Cited

U.S. PATENT DOCUMENTS

| | | | |
|---|---|---|---|
| 3,973,036 | 8/1976 | Hirano | 560/124 |
| 4,024,163 | 5/1977 | Elliott | 260/347.4 |
| 4,130,657 | 12/1978 | Plummer | 424/305 |
| 4,152,455 | 5/1979 | Engel | 560/124 |
| 4,214,004 | 7/1980 | Plummer | 424/305 |
| 4,263,319 | 4/1981 | Engel | 560/124 |
| 4,329,518 | 5/1982 | Plummer | 568/807 |
| 4,333,950 | 6/1982 | Engel | 424/305 |
| 4,402,973 | 9/1983 | Plummer | 560/124 |

FOREIGN PATENT DOCUMENTS 2083025  3/1982  United Kingdom .

OTHER PUBLICATIONS

Elliott, Pestic. Sci., 6, pp. 537–542, (1975).
Brown, J. Agr. Food Chem., 23, pp. 115–117, (1975).
Norton, Botyu-Kagaku, 41, pp. 1–7, (1976).

*Primary Examiner*—Michael L. Shippen
*Attorney, Agent, or Firm*—R. L. Andersen; H. R. Ertelt; W. Schmonsees

[57] ABSTRACT

Difluoroethenylcyclopropanecarboxylates of the formula

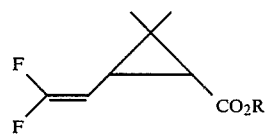

in which R is a selected biphenylmethyl, bridged biphenylmethyl or 4-phenyl-2-indanyl group, having a high level of activity against acarids are disclosed.

6 Claims, No Drawings

ACARICIDAL DIFLUOROETHENYLCYCLOPROPANECARBOXYLATES

This application is a continuation, of application Ser. No. 474,366, filed 3/11/83, now abandoned.

The present invention relates to pyrethroids exhibiting high insecticidal activity and unexpectedly high acaricidal activity. More specifically, the invention relates to selected difluoroethenylcyclopropanecarboxylates, insecticidal and acaricidal compositions thereof, and to a method for controlling insects and acarids.

Various dihalovinylcyclopropanecarboxylates have been described. M. Elliott et al., J. Pesti. Sci., 6, 537–42 (1975) discloses the insecticidal activity of various dibromoethenyl, dichloroethenyl, and difluoroethenylcyclopropanecarboxylic acid esters, and that, in general, the dichloroethenyl and dibromoethenyl esters are more active than those containing a difluoroethenyl group. The compounds described in that publication are the subject of U.S. Pat. No. 4,024,163.

Since that time numerous other insecticidal dichloroethenyl, dibromoethenyl, and difluoroethenylcyclopropanecarboxylate esters have been reported, a few of which are said to have some acaricidal activity.

Quite surprisingly, it has been found that certain esters of 3-(2,2-difluoroethenyl)-2,2-dimethylcyclopropanecarboxylic acid exhibit unexpectedly high levels of acaricidal activity when compared with the corresponding dichloro and dibromo analogs.

The compounds having the unusual acaricidal properties described above are cyclopropanecarboxylic acid derivatives of the general formula

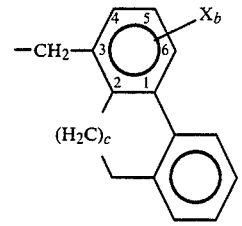

I in which

R is an alcohol moiety selected from:
(A) a biphenylmethyl group of the formula

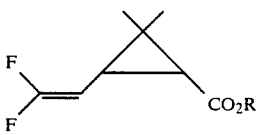

(B) a bridged biphenylmethyl group of the formula

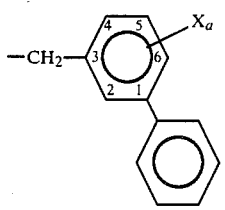

(C) a 4-phenyl-2-indanyl group
in which
X is selected from hydrogen; halogen especially fluorine, chlorine, and bromine; lower ($C_{1-6}$) alkyl; lower haloalkyl; and lower alkoxy; a is 0 to 4; b is 0 to 3; and c is 1 to 3.

The present invention also includes all isomeric and enantiomeric forms of the acid and alcohol moieties, including, but not limited to, the cis isomers, trans isomers, 1R-cis isomers, 1S-cis isomers, and all mixtures thereof. The examples set forth illustrate various methods for preparing the compounds of this invention and the physical constants for the resulting compounds and intermediates.

EXAMPLE 1

(2,4-Dimethyl[1,1'-biphenyl]-3-yl)methyl 1R,cis-3-(2,2-difluoroethenyl)-2,2-dimethylcyclopropanecarboxylate (Compound 1)

Step A
1R,cis-3-(2,2-Difluoroethenyl)-2,2-dimethyl-cyclopropanecarboxylic acid A stirred solution of 0.56 g (16.0 mmole) of (5-benzyl-3-furyl)methyl 1R,cis-3-(2,2-difluoroethenyl)-2,2-dimethylcyclopropanecarboxylate and 5 ml of a 10% aqueous sodium hydroxide solution in 5 ml of methanol was heated at 80° C. for three hours. The reaction mixture was evaporated under reduced pressure to leave a liquid residue. The residue was diluted with 15 ml of water and the resultant solution washed with diethyl ether. The aqueous phase was acidified to a pH of about 2 with concentrated hydrochloric acid. The acidic mixture was extracted with diethyl ether. The extract was washed with water, dried over anhydrous sodium sulfate and filtered. The filtrate was evaporated under reduced pressure to yield 0.22 g of 1R,cis-3-(2,2-difluoroethenyl-2,2-dimethylcyclopropanecarboxylic acid as an oil.

Step B (2,4-Dimethyl[1,1'-biphenyl]-3-yl)methyl 1R,cis-3-(2,2-difluoroethenyl)-2,2-dimethylcyclopropanecarboxylate A stirred solution of 0.2 g (1.14 mmole) of 1R,cis-3-(2,2-difluoroethenyl)-2,2-dimethylcyclopropanecarboxylic acid and one drop of dry N,N-dimethylformamide in 10 ml of dry diethyl ether was cooled to 0° C. While at 0° C., 0.22 g (1.71 mmole) of oxalyl chloride was added. The resultant mixture was allowed to warm to room temperature during a one hour period, at which time the mixture was evaporated under reduced pressure to leave a yellow oil. The oil was dissolved in 2 ml of dry diethyl ether and added to a stirred solution of 0.16 g (1.6 mmole) of triethylamine and 0.34 g (1.6 mmole) of 2,4-dimethyl[1,1'-biphenyl]-3-methanol in 20 ml of dry diethyl ether at 0° C. The reaction mixture was allowed to warm to room temperature and stirred for approximately 18 hours. The mixture was poured into 25 ml of water and the organic phase separated. The organic phase was washed with 10 ml of water, dried over anhydrous magnesium sulfate and filtered. The filtrate was evaporated under reduced pressure to give a yellow oil. The oil was purified by chromatography on a Chromatotron (U.S. Pat. No. 4,139,458) using a 2 mm silica gel plate, eluted with diethyl ether:hexanes (5:95), to yield 0.066 g of (2,4-dimethyl[1,1'-biphenyl]-3-yl)methyl 1R-cis-3-(2,2-difluoroethenyl)-2,2-dimethylcyclopropanecarboxylate as an oil.

NMR (CDCl$_3$, ppm): 1.20(s,3H); 1.25(s,3H); 1.60–1.85(m,2H); 2.25(s,3H); 2.42(s,3H); 4.40–4.90(m,1H); 5.25(s,2H); 7.05–7.50(m,7H).

EXAMPLE 2

(2,4,5,6-Tetrafluoro[1,1'-biphenyl]-3-yl)methyl trans-3-(2,2-difloroethenyl)-2,2-dimethylcyclopropanecarboxylate (Compound 2)

Step A Ethyl trans-3-(2,2-difluoroethenyl)-2,2-dimethylcyclopropanecarboxylate A stirred solution of 24.1 g (0.14 mole) of ethyl cis,-trans-2,2-dimethyl-3-formylcyclopropanecarboxylate and 44.5 g (0.17 mole) of triphenylphosphine in 150 ml of N,N-dimethylformamide was heated at 156° C. During a 20 minute period 32.0 g (0.19 mole) of sodium chlorodifluoroacetate was added to the hot solution. After complete addition, the reaction was stirred at 100° C. for two hours, then cooled and poured into 750 ml of water. The resultant mixture was extracted with three 175 ml portions of diethyl ether. The extracts were combined, washed with water, dried over anhydrous magnesium sulfate and filtered The filtrate was evaporated under reduced pressure to give a residue. The residue was chromatographed on silica gel, eluted with ethyl acetate:hexanes (5:95), to give an oil. The oil was purified by distillation under reduced pressure to yield 13.6 g of ethyl trans-3-(2,2-difluoroethenyl-2,2-dimethylcyclopropanecarboxylate as an oil (b.p. 75°–81° C./14 mmHg).

Step B trans-3-(2,2-Difluoroethenyl)-2,2-dimethylcyclopropanecarboxylic acid A stirred solution of 10.0 g (0.049 mole) of ethyl trans-3-(2,2-difluoroethenyl)-2,2-dimethylcyclopropanecarboxylate and 30 ml of a 10% aqueous sodium hydroxide solution in 60 ml of ethanol was heated at reflux for 1.25 hours, then stirred at room temperature for approximately 18 hours. The reaction mixture was heated at 70° C. for an additional 1.5 hours, then cooled to room temperature and poured into 150 ml of a 5% aqueous hydrochloric acid solution. The resultant mixture was extracted with three 50 ml portions of diethyl ether. The extracts were combined, washed twice with water (50 ml) and once with a saturated aqueous sodium chloride solution, then dried over anhydrous magnesium sulfate. The organic solution was filtered, and the filtrate evaporated under reduced pressure to yield 7.95 g of trans-3-(2,2-difluoroethenyl)-2,2-dimethylcyclopropanecarboxylic acid as an oil.

Step C trans-3-(2,2-Difluoroethenyl)-2,2-dimethylcyclopropanecarbonyl chloride A stirred solution of 2.0 g (0.0114 mole) of trans-3-(2,2-difluoroethenyl)-2,2-dimethylcyclopropanecarboxylic acid and 0.08 g of N,N-dimethylformamide in 20 ml of dry diethyl ether was cooled to 0° C. A solution of 2.17 g (0.017 mole) of oxalyl chloride in 2 ml of dry diethyl ether was added to the reaction mixture during a 20 minute period. Upon complete addition the mixture was allowed to warm to room temperature and stirred for two hours. The mixture was concentrated under reduced pressure to give a yellow oil. The oil was dissolved in 5 ml of dry diethyl ether and the solvent removed under reduced pressure to yield trans-3-(2,2-difluoroethenyl)-2,2-dimethylcyclopropanecarbonyl chloride as an oil.

Step D (2,4,5,6-Tetrafluoro[1,1'-biphenyl]-3-yl)methyl trans-3-(2,2-difluoroethenyl)2,2-dimethylcyclopropanecarboxylate To a stirred solution of 0.97 g (3.8 mmole) of 2,4,5,6-tetrafluoro[1,1'-biphenyl]-3-methanol and 1 ml of dry triethylamine in 8 ml of dry diethyl ether was added 4 ml of a dry diethyl ether solution of trans-3-(2,2-difluoroethenyl)-2,2-dimethylcyclopropanecarbonyl chloride (0.95 mmole/ml). The resultant mixture was stirred at room temperature for approximately 18 hours, then poured into 50 ml of water. The organic phase was separated, washed with a 5% aqueous sodium bicarbonate solution followed by a water wash, then dried over anhydrous magnesium sulfate. The organic phase was filtered, and the filtrate evaporated under reduced pressure to give an oil. The oil was purified by column chromatography on silica gel, eluted with ethyl acetate:hexanes (10:90), to yield 0.92 g of (2,4,5,6-tetrafluoro[1,1'-biphenyl]-3-yl)methyl trans-3-(2,2-difluoroethenyl)-2,2-dimethylcyclopropanecarboxylate as a solid (m.p. 69°–72° C.).

NMR (CDCl$_3$, ppm): 1.13(s,3H); 1.27(s,3H); 1.47(d,J=5 Hz,1H); 1.91–2.12(m,1H); 4.03(ddd,J=3,8,25 Hz,1H); 5.25(t,J=1.5 Hz,2H); 7.43(bs,5H).

EXAMPLE 3

By the method of Example 2, (2-methyl[1,1'-biphenyl]-3-yl)methyl trans-3-(2,2-difluoroethenyl)-2,2-dimethylcyclopropanecarboxylate (Compound 3) was prepared from trans-3-(2,2-difluoroethenyl)-2,2-dimethylcyclopropanecarbonyl chloride and 2-methyl-[1,1'-biphenyl]-3-methanol; yield 0.98 g as an oil.

NMR (CDCl$_3$, ppm): 1.15(s,3H); 1.27(s,3H); 1.53(d,J=5 Hz,1H); 1.93–2.18(m,1H); 2.22(s,3H); 4.02(ddd,J=3,8, 25 Hz,1H); 5.22(s,2H), 7.20–7.45(m,8H).

EXAMPLE 4

By the method of Example 2, the reaction of trans-3-(2,2-difluoroethenyl)-2,2-dimethylcyclopropanecarbonyl chloride with 2,4-dimethyl[1,1'-biphenyl]-3-methanol produced 0.78 g of (2,4-dimethyl[1,1'-biphenyl]-3-yl)methyl trans-3-(2,2-difluoroethenyl)-2,2-dimethylcyclopropanecarboxylate (Compound 4) as an oil.

NMR (CDCl$_3$, ppm): 1.12(s,3H); 1.30(s,3H); 1.50(d,J=5 Hz,1H); 1.92–2.20(m,1H); 2.27(s,3H), 2.43(s,3H); 4.06(ddd,J=3,8,25 Hz,1H); 5.28(s,2H); 7.10–7.40(m,7H).

EXAMPLE 5

By the method of Example 2, the reaction of trans-3-(2,2-difluoroethenyl)-2,2-dimethylcyclopropanecarbonyl chloride with 4-phenyl-2-indanol produced 0.82 g of 4-phenyl-2-indanyl trans-3-(2,2-difluoroethenyl)-2,2-dimethylcyclopropanecarboxylate (Compound 5) as an oil.

NMR (CDCl₃, ppm): 1.07(s,3H); 1.22(s,3H); 1.49(d,J=4Hz,1H), 1.92-2.13(m,1H); 3.00-3.20(m,4H), 4.02(ddd,J=3,8,25 Hz,1H); 5.35-5.70(m,1H), 7.18-7.50(m,8H).

EXAMPLE 6

By the method of Example 2, 0.83 g of (6,7-dihydro-5H-dibenzo[a,c]cyclohepten-4-yl)methyl trans-3-(2,2-difluoroethenyl)-2,2-dimethylcyclopropanecarboxylate (Compound 6) was produced from trans-3-(2,2-difluoroethenyl)-2,2-dimethylcyclopropanecarbonyl chloride and 6,7-dihydro-5H-dibenzo[a,c]cycloheptene-4-methanol.

NMR (CDCl₃, ppm): 1.10(s,3H); 1.27(s,3H); 1.53(d,J=6 Hz,1H); 1.80-2.90(m,7H), 4.01(ddd,J=3,8,25 Hz,1H); 5.20(s,2H); 7.15-7.40(m,7H).

The following example illustrates preparation of the lower alkyl ester as an intermediate which may then be converted to the compound of the invention by methods well known to those skilled in the art, for example by reaction with an alcohol of the formula HOR in which R is as defined above, or by forming the free acid and converting it to the acid halide and reacting that with the alcohol, or by reacting a salt of the acid with a compound of the formula X-R in which X is a good leaving group such as a bromide or chloride. The intermediate is a cis, trans ester from which the individual isomers may be recovered by known means, if desired.

EXAMPLE 7

Ethyl cis,trans-3-(2,2-difluoroethenyl)-2,2-dimethylcyclopropanecarboxylate

Step A Ethyl 4,6-dibromo-6,6-difluoro-3,3-dimethylhexanoate

Under a dry nitrogen atmosphere a stirred solution of 22.3 g (0.134 mole) of ethyl 3,3-dimethyl-4-pentenoate, 50.95 g (0.242 mole) of dibromodifluoromethane, 0.31 g (0.0014 mole) of copper (I) bromide and 4.1 g (0.067 mole) of ethanolamine in 135 ml of dry tert-butanol was heated at reflux for 15 hours. The reaction mixture was cooled to room temperature, poured into 300 ml of water then extracted with three 75 ml portions of diethyl ether. The extracts were combined and washed in succession with water and a saturated aqueous sodium chloride solution. The organic phase was dried over anhydrous magnesium sulfate, filtered, and the filtrate evaporated under reduced pressure to leave an oil. The oil was purified by distillation under reduced pressure to yield 8.3 g of ethyl 4,6-dibromo-6,6-difluoro-3,3-dimethylhexanoate as an oil (b.p. 80°-92° C./1 mmHg).

Step B Ethyl cis,trans-3-(2,2-difluoroethenyl)-2,2-dimethylcyclopropanecarboxylate Under a dry nitrogen atmosphere a solution consisting of 3.54 g (0.01 mole) of ethyl 4,6-dibromo-6,6-difluoro-3,3-dimethylhexanoate in 25 ml of dry tetrahydrofuran was added to a stirred mixture of 2.48 g (0.022 mole) of potassium tertbutoxide in 25 ml of tetrahydrofuran cooled to −5° C. After complete addition the reaction mixture was stirred at −5° C. for four hours, then allowed to warm to room temperature and stirred for two hours. Aqueous saturated ammonium chloride was added to the reaction mixture until a pH of about 7 was obtained. The resultant mixture was extracted with diethyl ether; the extract was dried over anhydrous magnesium sulfate; then filtered. The filtrate was evaporated under reduced pressure to give an oil. Gas chromatographic analysis of the oil indicated 65% ethyl cis,trans-3-(2,2-difluoroethenyl)-2,2-dimethylcyclopropanecarboxylate (cis:trans ratio 46:54). The oil was dissolved in 50 ml of dry tetrahydrofuran and 1.83 g of 1,8-diazabicyclo-[5.4.0]undec7-ene was added. This mixture was stirred under a nitrogen atmosphere at reflux for approximately 18 hours. The mixture was cooled to room temperature, diluted with diethyl ether and washed in succession with a cold 5% aqueous hydrochloric acid solution and water. The organic phase was dried over anhydrous magnesium sulfate and filtered. The filtrate was evaporated under reduced pressure to yield 0.67 g of ethyl cis,trans-3-(2,2-difluoroethenyl)-2,2-dimethylcyclopropanecarboxylate as an oil (gas chromatographic analysis indicated 51% product with a cis:trans ratio of 36:64.

In the method aspect of this invention, an effective insecticidal and acaricidal amount of the compound of formula I is applied to the locus where insect and acarid control is desired, i.e., to the pest itself, to the foliage or seeds of agricultural plants, to the soil in which agricultural crops are planted or are to be planted, or topically for veterinary application. The compounds are useful for the control of household, veterinary, and crop insects and mites and may be applied as technical material or as formulated product.

Typical formulations include compositions of the active ingredient in combination with an acceptable carrier or extender, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particularly agent used, the additives and carriers used, other active ingredients, and the desired mode of application. With due consideration to these factors the active ingredient may suitably be present by weight of the formulation at a concentration of about 0.01% up to about 99.5%, preferably 0.1% up to 95% or 99% of the formulation. Typically a compatible carrier or extender may comprise from about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

· Many variations of spraying, dusting, and controlled or slow release compositions of a type known in the art may be used by substituting or adding an insecticidal compound or compounds of this invention into the compositions known or apparent to the art.

The insecticidal compounds of this invention may be formulated and applied with other compatible active ingredients including nematicides, insecticides, acaricides, fungicides, plant regulators, herbicides, fertilizers, and the like.

In applying these compounds, whether alone or with other agricultural chemicals, an insecticidally and acaricidally effective amount of the active ingredient must be applied. While the application rate will vary widely depending on the choice of compound, formulation, mode of application, purpose of application, and other like factors, a suitable use rate for agricultural crops may be in the range of 0.005 to 3 k/ha, preferably 0.01 to about 1 k/ha.

The insecticidal compounds of this invention were tested for insecticidal and acaricidal activity as described below.

FOLIAR APPLICATION TEST

A solution was prepared containing the test compound (0.512 or 0.5 gm), 10 ml of acetone and 0.25% (0.029 gm) octylphenoxypolyethoxyethanol. This solution was diluted to 100 ml with water to give a solution having 512 ppm or 500 ppm (w/w) active ingredient. Aliquots of this solution were diluted with an appropriate amount of water to provide solutions containing various concentrations of active ingredient.

Test organisms and techniques were as follows: The activity against Mexican bean beetle (*Epilachna varivestis* Muls.), southern armyworm (*Spodoptera eridania* [Cram.]), and cabbage looper (*Trichoplusia ni* [Hubner]) was evaluated by spraying the leaves of pinto bean plants with the test solution and infesting with 3rd instar larvae after the foliage had dried. The activity against twospotted spider mite (*Tetranychus urticae* [Koch]) was evaluated on pinto bean plants the leaves of which were sprayed with test solution after infestation with adult mites. To prevent escape of the insects from the test site, the complete test plant or the incised leaves were placed in capped paper cups. The tests were transferred to a holding room at 26.7° C. and 50% relative humidity for an exposure period of 48 hours. At the end of this time the dead and living insects were counted and the percent kill was calculated. Results of these tests are summarized in Table I below.

The compounds of this invention are numbered 1 through 6 in the Table. For purposes of comparison the corresponding dichloroethenyl (A) and/or dibromoethenyl (B) analog of the compound of the invention was included in the test. These compounds are identified as follows:

| Compound No. | Name |
|---|---|
| 1A | (2,4-dimethyl[1,1'-biphenyl]-3-yl)methyl 1R,cis-3-(2,2-dichloroethenyl)-2,2-dimethylcyclopropanecarboxylate |
| 2B | (2,4,5,6-tetrafluoro[1,1'-biphenyl]-3-yl)methyl trans-3-(2,2-dibromoethenyl)-2,2-dimethylcyclopropanecarboxylate |
| 3A | (2-methyl[1,1'-biphenyl]-3-yl)methyl trans-3-(2,2-dichloroethenyl)-2,2-dimethylcyclopropanecarboxylate |
| 3B | (2-methyl[1,1'-biphenyl]-3-yl)methyl trans-3-(2,2-dibromoethenyl)-2,2-dimethylcyclopropanecarboxylate |
| 4A | (2,4-dimethyl[1,1'-biphenyl]-3-yl)methyl trans-3-(2,2-dichloroethenyl)-2,2-dimethyl-cyclopropanecarboxylate |
| 6A | (6,7-dihydro-5H—dibenzo[a,c]cyclohepten-4-yl)methyl trans-3-(2,2-dichloroethenyl)-2,2-dimethylcyclopropanecarboxylate |

In Table I, compounds 2 through 5 of the invention are approximately comparable in insecticidal activity (southern armyworm, cabbage looper, and Mexican bean beetle) to the corresponding dichloro and/or dibromo analog, but are vastly superior against twospotted spider mite. The 1R-cis compound is superior in both respects to the 1R-cis dichloroethenyl analog.

TABLE I

Foliar Application Testing

| Compound No. | Rate (ppm) | SAW[a] | CL[a] | TSM[a] | MBB[a] |
|---|---|---|---|---|---|
| 1 | 16.0 | — | — | 100 | — |
|  | 8.0 | 100 | 100 | 100 | — |
|  | 4.0 | 100 | 100 | 100 | 100 |
|  | 2.0 | 100 | 95 | 100 | 100 |
|  | 1.0 | 95 | 90 | 100 | 85 |
|  | 0.5 | 95 | 90 | — | 85 |
|  | 0.25 | — | — | — | 65 |
| 1A | 64.0 | 100 |  | 0 @ 500 ppm | 65 |
|  | 48.0 | — |  |  | 70 |
|  | 32.0 | — |  |  | 55 |
|  | 16.0 | 100 | 100 |  | 55 |
|  | 8.0 | — |  |  | 30 |
|  | 4.0 |  | 88 |  |  |
|  | 2.0 |  | 78 |  |  |
|  | 1.0 |  | 50 |  |  |
|  | 0.5 |  | 35 |  |  |
|  | 0.25 |  | 5 |  |  |
| 2 | 64.0 | 100 |  | 83 | 100 |
|  | 16.0 | 95 |  | 29 | 75 |
|  | 8.0 | 70 |  | 14 | 55 |
|  | 4.0 | 35 |  | 1 | 50 |
|  | 2.0 | 5 |  | 0 | 10 |
| 2B | 64.0 | 100 |  | 0 | 100 |
|  | 24.0 | — |  | — | — |
|  | 16.0 | 100 |  | 0 | 100 |
|  | 10.0 | 65 |  |  | — |
|  | 6.5 | 55 |  |  | 100 |
|  | 4.5 | 5 |  |  | 88* |
|  | 3.2 |  |  |  | 75 |
|  | 2.1 |  |  |  | 63* |
|  | 1.4 |  |  |  | 65 |
| 3 | 64.0 | 100 |  | 67 | 100 |
|  | 16.0 | 80 |  | 29 | 90 |
|  | 8.0 | 45 |  | 9 | 55 |
|  | 4.0 | 20 |  | 0 | 15 |
|  | 2.0 | 15 |  | 0 | 10 |
| 3A | 64.0 | 100 |  | 0 | 100 |
|  | 16.0 | 80* |  | 0 | 80 |
|  | 10.0 | 20 |  |  | 100 |
|  | 6.5 | 10 |  |  | 75 |
|  | 4.5 | 0 |  |  | 60 |
|  | 3.2 | — |  |  | 35 |
| 3B | 64.0 | 100 |  | 0 @ 500 ppm | 100 |
|  | 16.0 | 80** |  |  | 72** |
|  | 8.0 | 50* |  |  | 40* |
|  | 4.0 | 13* |  |  | 23* |
|  | 2.0 | — |  |  | 5 |
|  | 1.0 | 5 |  |  | — |
| 4 | 64.0 | 100 |  | 75 | 85 |
|  | 16.0 | 95 |  | 17 | 75 |
|  | 8.0 | 80** |  | 0 | 60 |
|  | 4.0 | 63** |  | 0 | 50 |
|  | 2.0 | 32** |  | 0 | 25 |
| 4A | 64.0 | 100 |  | 0 | 100 |
|  | 48.0 | — |  | — | 95 |
|  | 32.0 | — |  | — | 90 |
|  | 16.0 | 100 |  | 0 | 80 |
|  | 8.0 | 85 |  |  |  |
|  | 4.0 | 25 |  |  |  |
|  | 2.0 | 5 |  |  |  |

TABLE I-continued

| Foliar Application Testing | | | | | |
|---|---|---|---|---|---|
| Compound | Rate | Percent Kill | | | |
| No. | (ppm) | SAW[a] | CL[a] | TSM[a] | MBB[a] |
| 5 | 64.0 | 95 | | 90 | 95 |
|  | 16.0 | 80 | | 40 | 90 |
|  | 8.0 | 55 | | 25 | 40 |
|  | 4.0 | 0 | | 9 | 5 |
|  | 2.0 | 0 | | 1 | 0 |
| 6 | 64.0 | 100 | | 77 | 70 |
|  | 26.0 | 95 | | 17 | 30 |
|  | 8.0 | 40 | | 0 | 0 |
|  | 4.0 | 20 | | 0 | 0 |
|  | 2.0 | 5 | | 0 | 0 |
| 6A | 64.0 | 90 | | 50 @ 500 ppm | 90 |
|  | 32.0 | — | | | 100 |
|  | 16.0 | 93* | | | 73* |
|  | 8.0 | 30 | | | 25 |
|  | 4.0 | 10 | | | 20 |

[a]Test Species:
SAW = southern armyworm (*Spodoptera eridania*)
CL = cabbage looper (*Trichoplusia ni*)
TSM = twospotted spider mite (*Tetranychus urticae*)
MBB = Mexican bean beetle (*Epilachna varivestis*)
*Average of two tests
**Average of three tests

We claim:

1. A compound of the formula

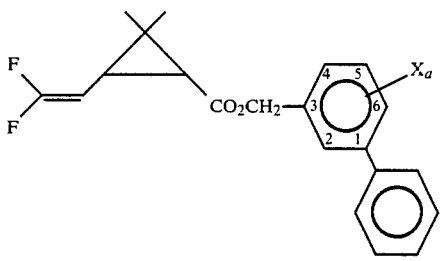

in which $X_a$ is 2-fluoro, 2,4-difluoro, 2,4,6-trifluoro, 2,4,5,6-tetrafluoro, 2-methyl, or 2,4-dimethyl.

2. The compound of claim 1 in which $X_a$ is 2-methyl.

3. An acaricidal composition comprising an acaricidally effective amount of a compound of the formula

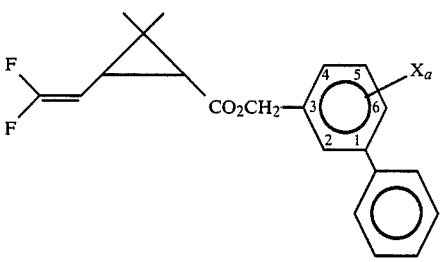

in which $X_a$ is 2-fluoro, 2,4-difluoro, 2,4,6-trifluoro, 2,4,5,6-tetrafluoro, 2-methyl, or 2,4-dimethyl in admixture with an agriculturally acceptable carrier.

4. The composition of claim 3, employing the compound in which $X_a$ is 2-methyl.

5. A method for controlling acarids in agricultural crops which comprises applying to the foliage of such agricultural crops an acaricidal amount of the compound

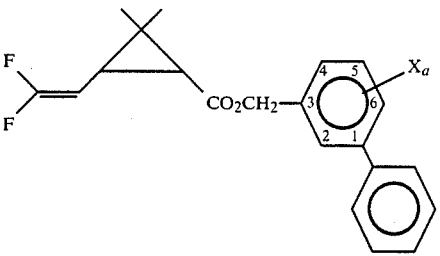

in which $X_a$ is 2-fluoro, 2,4-difluoro, 2,4,6-trifluoro, 2,4,5,6-tetrafluoro, 2-methyl, or 2,4-dimethyl.

6. The method of claim 5, employing the compound in which $X_a$ is 2-methyl.

* * * * *